United States Patent
Kumbhar

(10) Patent No.: US 11,053,232 B2
(45) Date of Patent: Jul. 6, 2021

(54) 1,3,5-DIOXAZINE DERIVATIVES, METHOD OF PREPARATION AND APPLICATION THEREOF AS SULFIDE SCAVENGER

(71) Applicant: Kishor Prabhakar Kumbhar, Maharashtra (IN)

(72) Inventor: Kishor Prabhakar Kumbhar, Maharashtra (IN)

(*) Notice: Subject to any disclaimer, the term of this patent is extended or adjusted under 35 U.S.C. 154(b) by 0 days.

(21) Appl. No.: 16/349,520

(22) PCT Filed: Jul. 5, 2017

(86) PCT No.: PCT/IB2017/054050
§ 371 (c)(1),
(2) Date: May 13, 2019

(87) PCT Pub. No.: WO2018/011673
PCT Pub. Date: Jan. 18, 2018

(65) Prior Publication Data
US 2019/0300515 A1    Oct. 3, 2019

(30) Foreign Application Priority Data
Jul. 9, 2016  (IN) .............................. 201621023569

(51) Int. Cl.
| | | |
|---|---|---|
| *C07D 413/14* | (2006.01) | |
| *C07D 273/01* | (2006.01) | |
| *C07D 413/10* | (2006.01) | |
| *C07D 413/12* | (2006.01) | |
| *C10G 29/20* | (2006.01) | |
| *A61L 2/20* | (2006.01) | |

(52) U.S. Cl.
CPC .............. *C07D 413/14* (2013.01); *A61L 2/20* (2013.01); *C07D 273/01* (2013.01); *C07D 413/10* (2013.01); *C07D 413/12* (2013.01); *C10G 29/20* (2013.01); *C10G 2300/207* (2013.01)

(58) Field of Classification Search
CPC .................................................... C07D 413/14
USPC ............................................................ 544/65
See application file for complete search history.

(56) References Cited

FOREIGN PATENT DOCUMENTS

| RU | 2485169 C1 * | 6/2013 |
| WO | 2001/014375 A1 | 3/2001 |
| WO | 2006/138147 A1 | 12/2006 |

OTHER PUBLICATIONS

English translation of RU-2485169-C1 (4 pages). (Jun. 2013).*
Claims in English of RU-2485169-C1 (1 page). (Jun. 2013).*
PUBCHEM Summary for CID 70517920, "5,5'-(Ethane-1,2-diyl)bis(1,3,5-dioxazinane)", U.S. National Library of Medicine (2012) pp. 1-11 (available at pubchem.ncbi.nlm.nih.gov/compound/70517920).
PUBCHEM Summary for CID 13743612, "2-(1,3,5-Dioxazinan-5-yl)ethanamine", U.S. National Library of Medicine (2007) pp. 1-9 (available at pubchem.ncbi.nlm.nih.gov/compound/13743612).

* cited by examiner

*Primary Examiner* — Kahsay Habte
(74) *Attorney, Agent, or Firm* — Robert C. Netter, Jr.; Dann, Dorfman, Herrell & Skillman

(57) ABSTRACT

The present disclosure relates to 1,3,5-dioxazine derivatives of formula (I) capable of reducing or eliminating hydrogen sulfide and other objectionable sulfides from oil field produced hydrocarbon fluids such as petroleum, fuel oil, gasoline, diesel, liquid propane, liquid butane, an aquaculture and production/processing of syngas/natural gas. The present disclosure further provides a method for preparing 1,3,5-dioxazine derivatives of formula I, and a method for scavenging sulfur-based species including, but not limited to hydrogen sulfide or alkyl/aryl mercaptans from a medium.

15 Claims, 11 Drawing Sheets

1,3,5-DIOXAZINE DERIVATIVES, METHOD OF PREPARATION AND APPLICATION THEREOF AS SULFIDE SCAVENGER

The present application is § 371 application of PCT/IB2017/054050, filed Jul. 5, 2017, which claims priority to IN Application No. 201621023569, filed Jul. 9, 2016. The entire disclosure of each of the foregoing applications is incorporated by reference herein.

FIELD OF THE INVENTION

The present disclosure pertains to 1,3,5-dioxazine compounds, preparation and methods of use thereof. The disclosed 1,3,5-dioxazine compounds are useful as scavengers of sulfur-based species, and more particularly as, hydrogen sulfide and/or mercaptan scavengers.

BACKGROUND

Background description includes information that may be useful in understanding the present invention. It is not an admission that any of the information provided herein is prior art or relevant to the presently claimed invention, or that any publication specifically or implicitly referenced is prior art. Any discussion of documents, acts, materials, devices, articles or the like that has been included in this specification is solely for the purpose of providing a context for the disclosure.

Oil field produced hydrocarbon fluids like crude oil, petroleum, fuel oil, gasoline, diesel, liquid propane, liquid butane, etc. that occur naturally in earth are often found to contain number of impurities such as carbon dioxide, sulfur, hydrogen sulfide, mercaptans, etc. Among other contaminants, organic sulfides such as hydrogen sulfide and mercaptans are toxic, corrosive and cause serious problems in both upstream and downstream oil and gas industries. Further, exposure to these organic sulfide gases, even at low concentrations, can cause serious injury or death.

There have been several scavengers reported in the art for reducing or essentially eliminating hydrogen sulfide and other objectionable sulfides from oil field produced fluids. For example, triazine based compounds are the most widely used sulfide scavenger for petroleum hydrocarbons, and are popular because of their relative safety, scavenging capacity, and low cost. In general, one mole of triazine compounds scavenges two moles of hydrogen sulfide. However, triazine based scavengers contain free formaldehyde, which is a known carcinogen and expected to cause health issues.

Although the application of sulfide scavengers is widely practiced in production and processing operations in the oil and gas industries, known scavengers have several limitations ranging from excessive prices to health, safety, handling and environmental problems. Apart from these shortcomings, triazines derived from MEA (monoethanolamine) forms stable emulsions and are responsible for scaling within the fluid lines. There is, thus, a continuing need in the art for alternative sulfide scavengers that overcome these deficiencies. The present invention satisfies the existing needs, as well as others, and generally overcomes the deficiencies found in the prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all markush groups used in the appended claims.

OBJECTS OF THE INVENTION

It is an object of the present disclosure to provide 1,3,5-dioxazine derivatives capable of reducing or eliminating hydrogen sulfide and other objectionable sulfides.

Another object of the present disclosure is to provide 1,3,5-dioxazine derivatives that can find utility in scavenging and/or reducing and/or eliminating hydrogen sulfide and other objectionable sulfides from oil field produced hydrocarbons.

It is a further object of the present disclosure to provide a method for preparing 1,3,5-dioxazine derivatives.

It is another object of the present disclosure to provide a simple and cost effective process for preparing 1,3,5-dioxazine derivatives that can be safely and easily scaled up.

It is another object of the present disclosure to provide a method for reducing or eliminating hydrogen sulfide and other objectionable sulfides from oil field produced hydrocarbon fluids.

SUMMARY

Aspects of the present disclosure relate to 1,3,5-dioxazine derivatives capable of reducing or eliminating hydrogen sulfide and other objectionable sulfides. The 1,3,5-dioxazine derivatives realized in accordance with embodiments of the present disclosure can find utility as "sulfide scavenger" in variety of applications including, in production and/or processing of oil field produced hydrocarbons such as crude oil, petroleum, fuel oil, gasoline, diesel, liquid propane, liquid butane and the likes, in production and/or processing of syngas/natural gas and in aquaculture, but not limited thereto.

In an aspect, the present disclosure provides a 1,3,5-dioxazine derivative having a structure of formula (I):

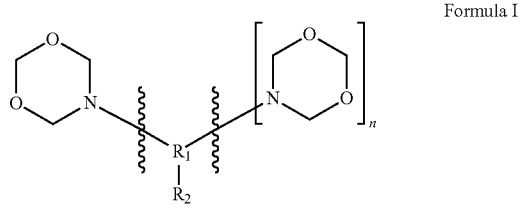

Formula I wherein:

"n" is a numeral from 0 to 10;

$R_1$ is substituted or unsubstituted amine group; or a substituted or unsubstituted, linear or branched, cyclic or acyclic $C_2$ to $C_{20}$ alkyl, $C_2$-$C_{28}$ thioether, $C_2$-$C_{28}$ alkanol, $C_2$-$C_{28}$ phosphorous containing alkyl or $C_2$-$C_{28}$ ether group; or a substituted or unsubstituted aromatic or heteroaromatic group; and $R_2$ is H, —OH, —SH, —NH$_2$, linear or branched $C_1$-$C_{15}$ alkyl group, aromatic, heteroaromatic, bridged ring, cycloalkyl, heteroalkyl, alkyl aromatic or a 1,3,5-dioxazine group.

In another aspect, the present disclosure provides a method for preparing the 1,3,5-dioxazine derivative of formula (I), the method including the step of reacting at least one amine compound with any or a combination of formaldehyde and paraformaldehyde under conditions effective to obtain the compound of formula (I). In an embodiment, the method includes reacting at least one amine compound with an aqueous solution containing a concentration of formaldehyde under conditions effective to obtain the compound of formula (I). In an embodiment, the method includes reacting at least one amine compound with an aqueous solution containing a concentration of paraformadehyde under conditions effective to obtain the compound of formula (I).

In an embodiment, the at least one amine compound that can be utilized in the methods of the present disclosure for the preparation of 1,3,5-dioxazine derivative of formula I can be selected from any or a combination of 1,2-Diaminoethane 1,3-Diaminopropane, 1,4-Diaminobutane, Tris(2-aminoethyl)amine, 1,4-Phenylenedimethanamine, N,N-Bis(2-aminoethyl)-1,2-ethanediamine, Diethylenetriamine, triethylenetetramine, polyalkylamines and mixture of various aliphatic, alicycic, cyclic and aromatic amines and derivatives thereof.

In another aspect, the present disclosure provides a method for reducing the amount of or eliminating hydrogen sulfide or alkyl/aryl mercaptan from a medium. The method includes contacting the medium with an effective amount of a compound of formula (I) of the present disclosure. In an embodiment, the medium is oil field produced hydrocarbon fluid, in another embodiment, the medium is aquaculture. In another embodiment, the medium is syngas or a natural gas.

Various objects, features, aspects and advantages of the inventive subject matter will become more apparent from the following detailed description of preferred embodiments.

BRIEF DESCRIPTION OF DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION OF THE INVENTION

Figure 1:
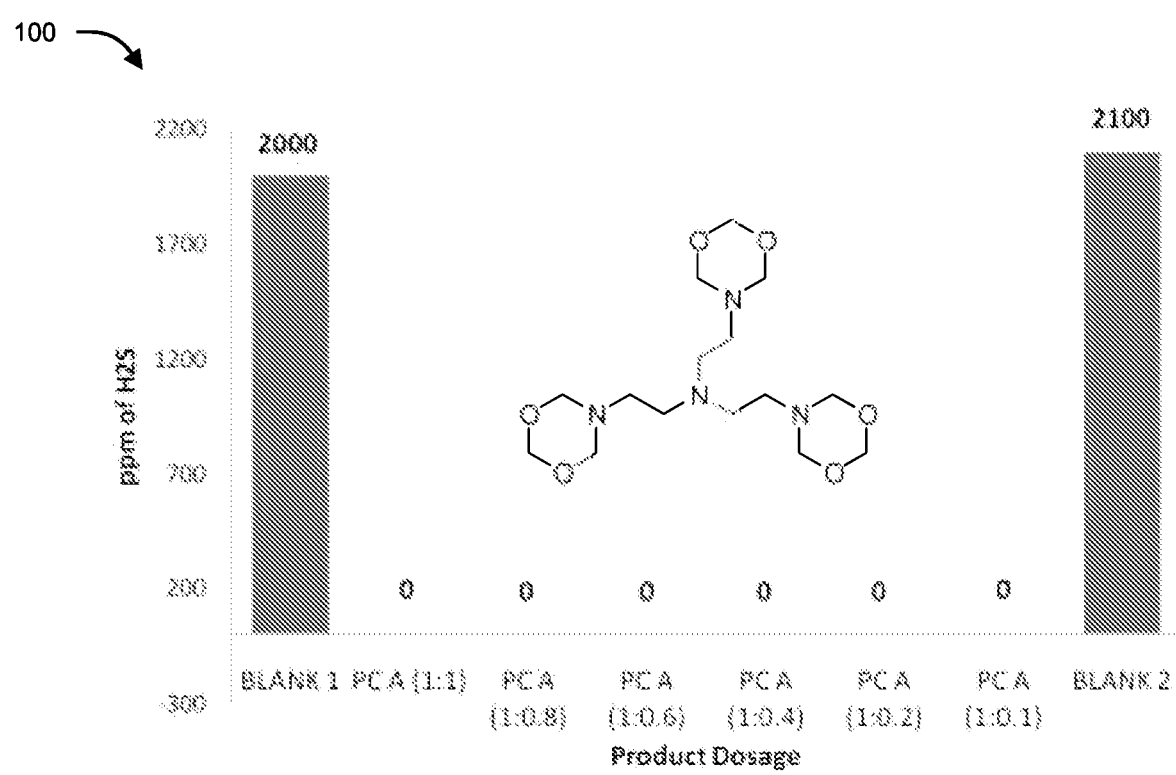
FIG. 1 is a graph illustrating hydrogen sulfide (H$_2$S) Scavenging performance of 1,3,5-dioxazine derivative of Formula II compared against blank, in accordance with embodiments of the present disclosure.
Figure 2:
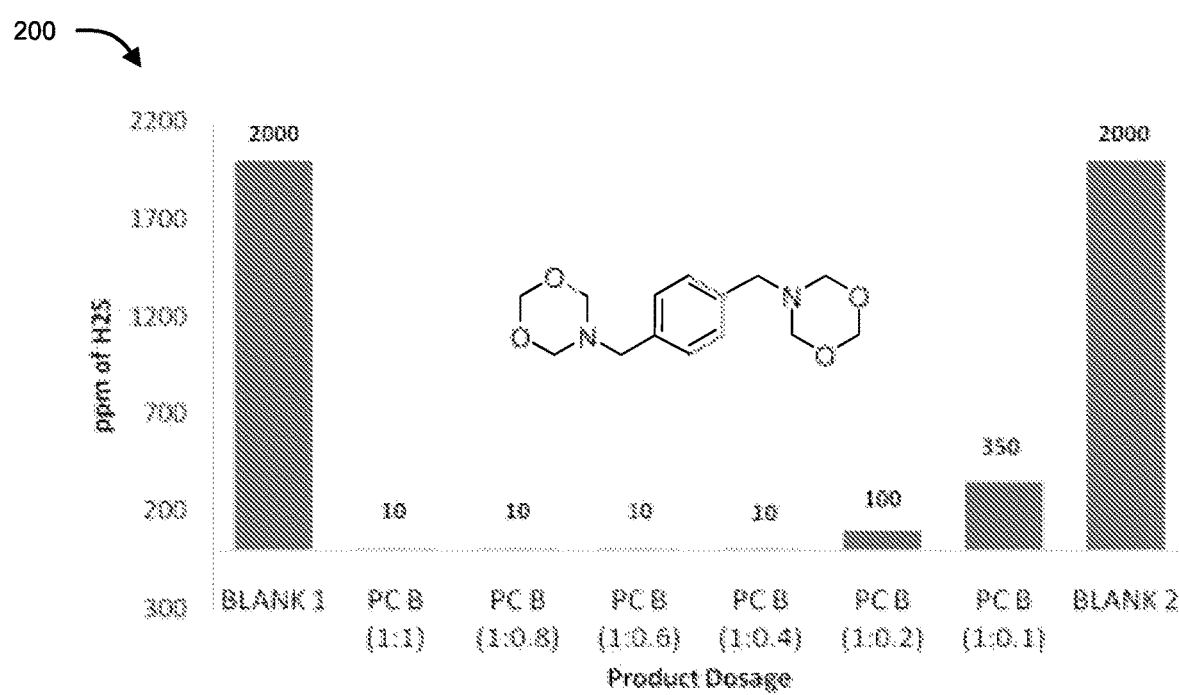
FIG. 2 is a graph illustrating H$_2$S Scavenging performance of 1,3,5-dioxazine derivative of Formula III compared against blank, in accordance with embodiments of the present disclosure.
Figure 3:
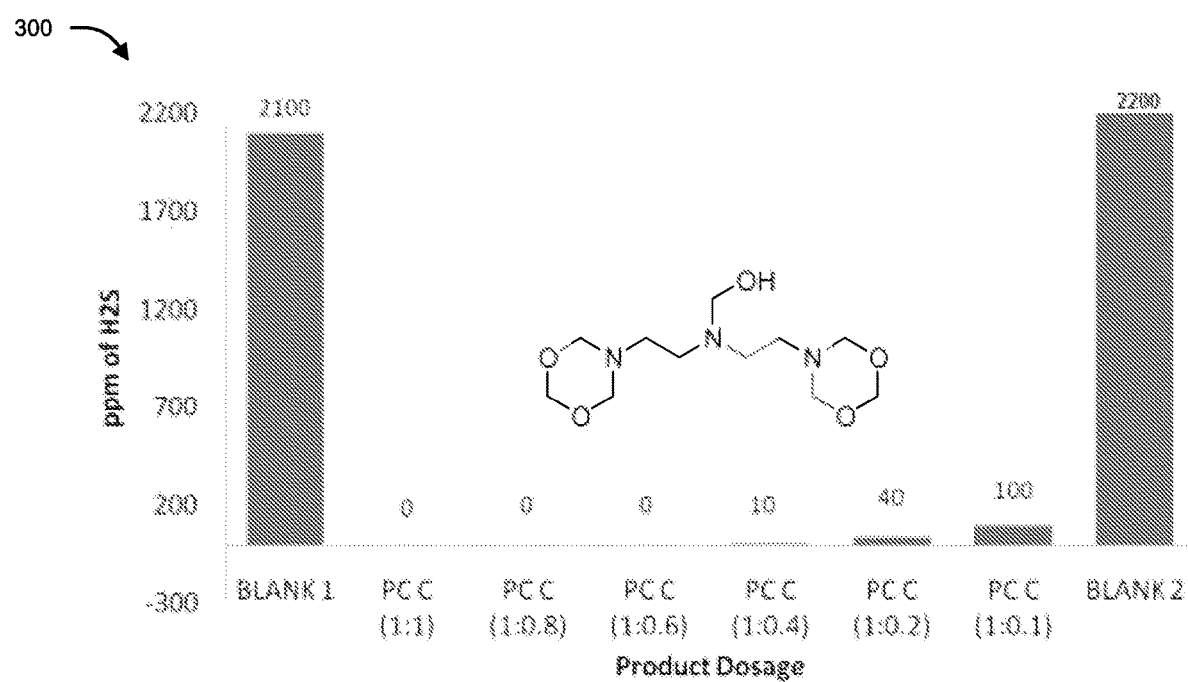
FIG. 3 is a graph illustrating H$_2$S Scavenging performance of 1,3,5-dioxazine derivative of Formula IV compared against blank, in accordance with embodiments of the present disclosure.
Figure 4:
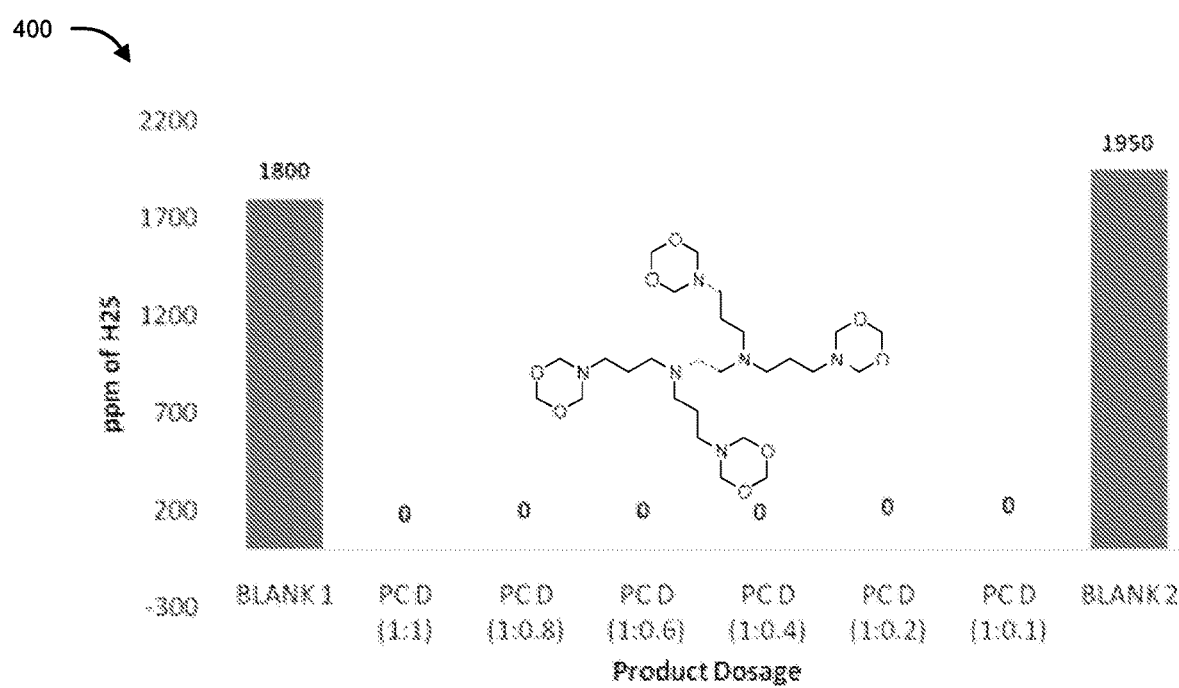
FIG. 4 is a graph illustrating H$_2$S Scavenging performance of 1,3,5-dioxazine derivative of Formula V compared against blank, in accordance with embodiments of the present disclosure.
Figure 5:
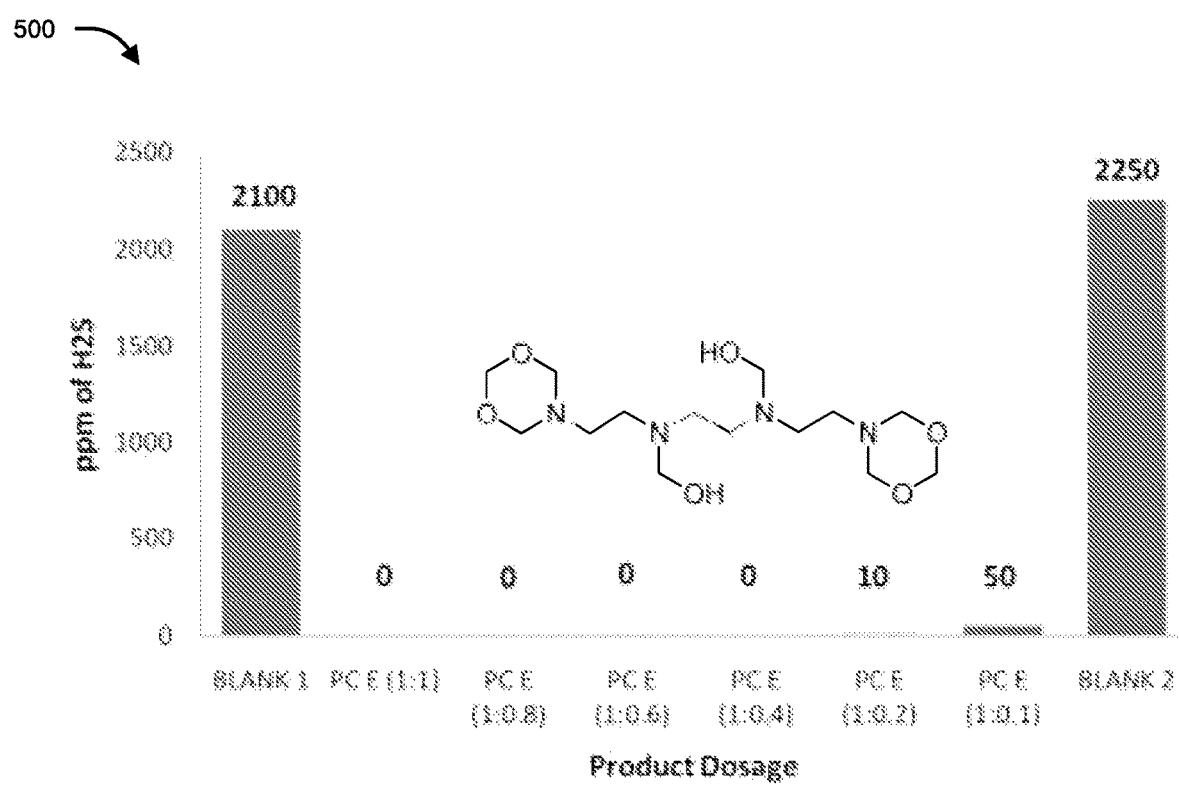
FIG. 5 is a graph illustrating H$_2$S Scavenging performance of 1,3,5-dioxazine derivative of Formula VI compared against blank, in accordance with embodiments of the present disclosure.
Figure 6:
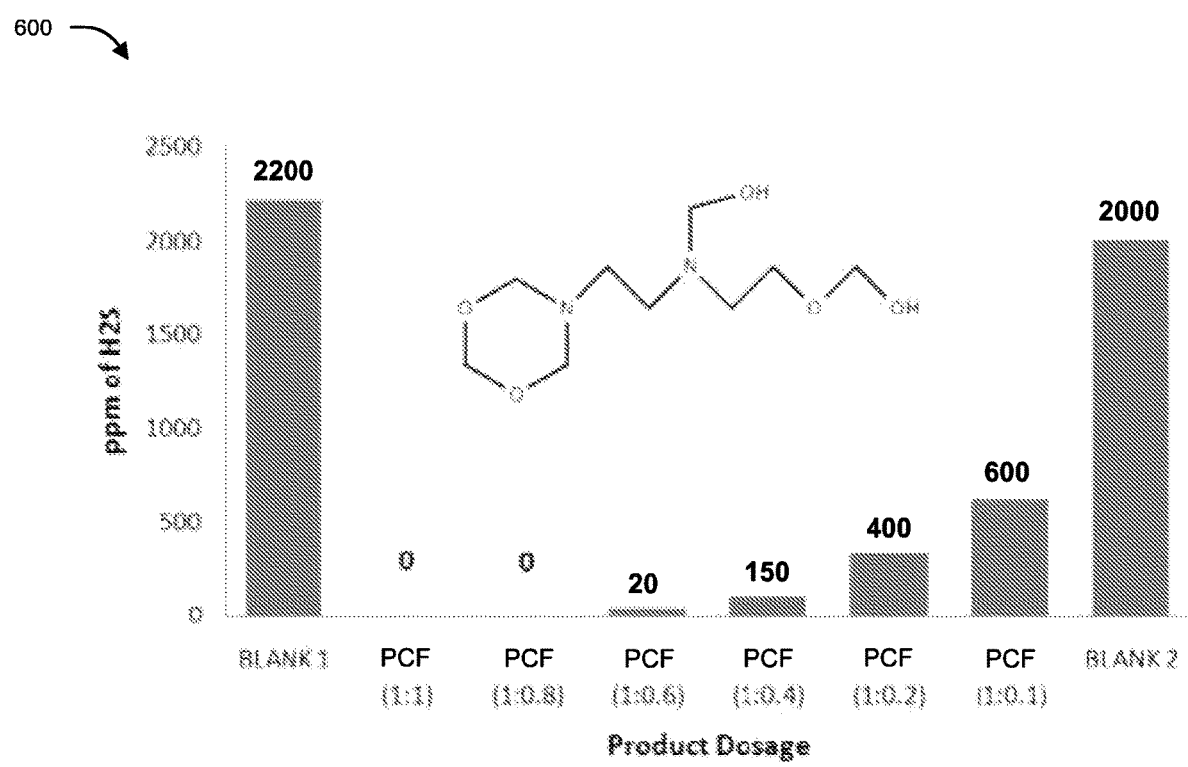
FIG. 6 is a graph illustrating H$_2$S Scavenging performance of 1,3,5-dioxazine derivative of Formula VII compared against blank, in accordance with embodiments of the present disclosure.
Figure 7:
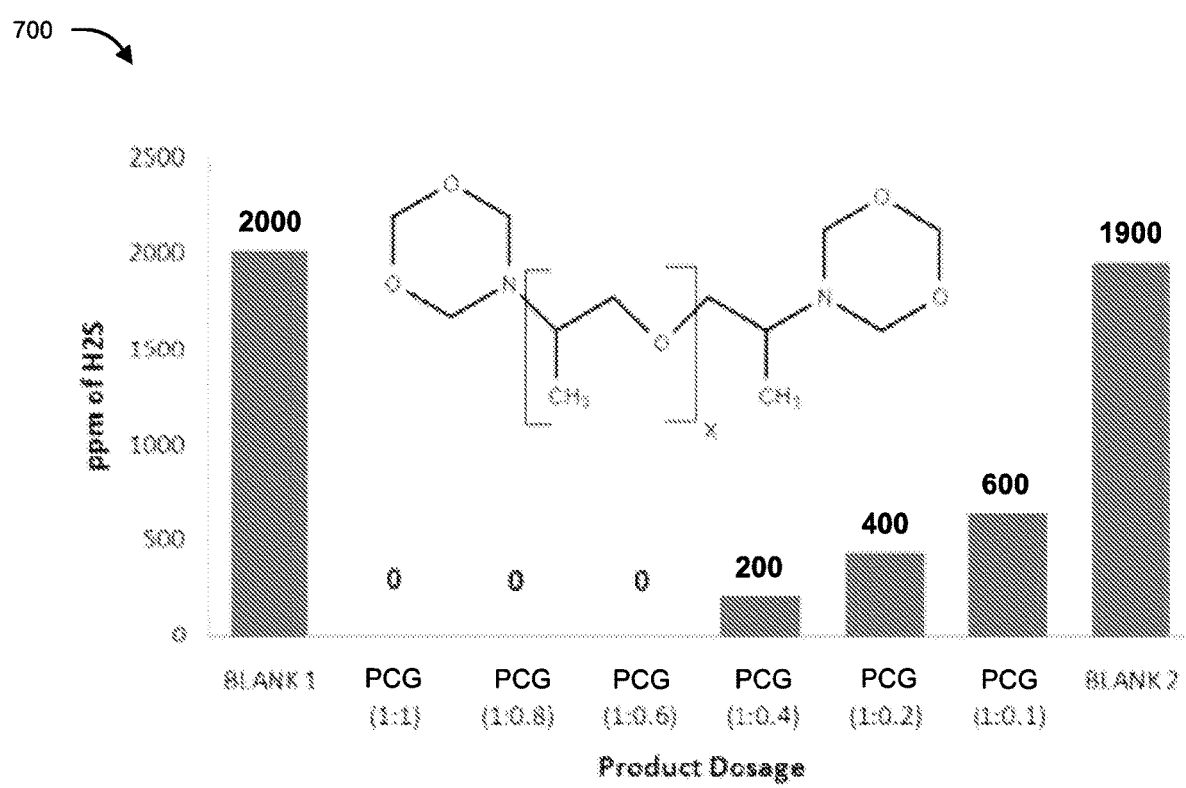
FIG. 7 is a graph illustrating H$_2$S Scavenging performance of 1,3,5-dioxazine derivative of Formula VIII compared against blank, in accordance with embodiments of the present disclosure.
Figure 8:
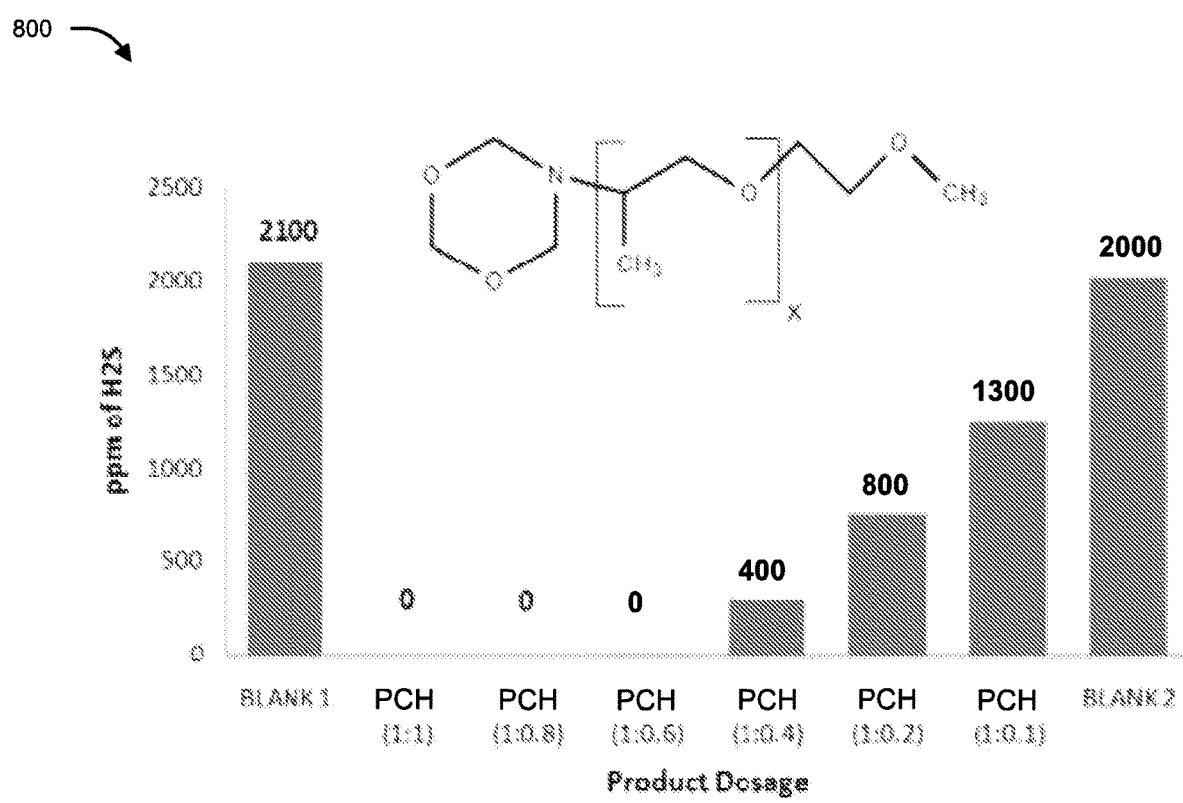
FIG. 8 is a graph illustrating H$_2$S Scavenging performance of 1,3,5-dioxazine derivative of Formula IX compared against blank, in accordance with embodiments of the present disclosure.
Figure 9:
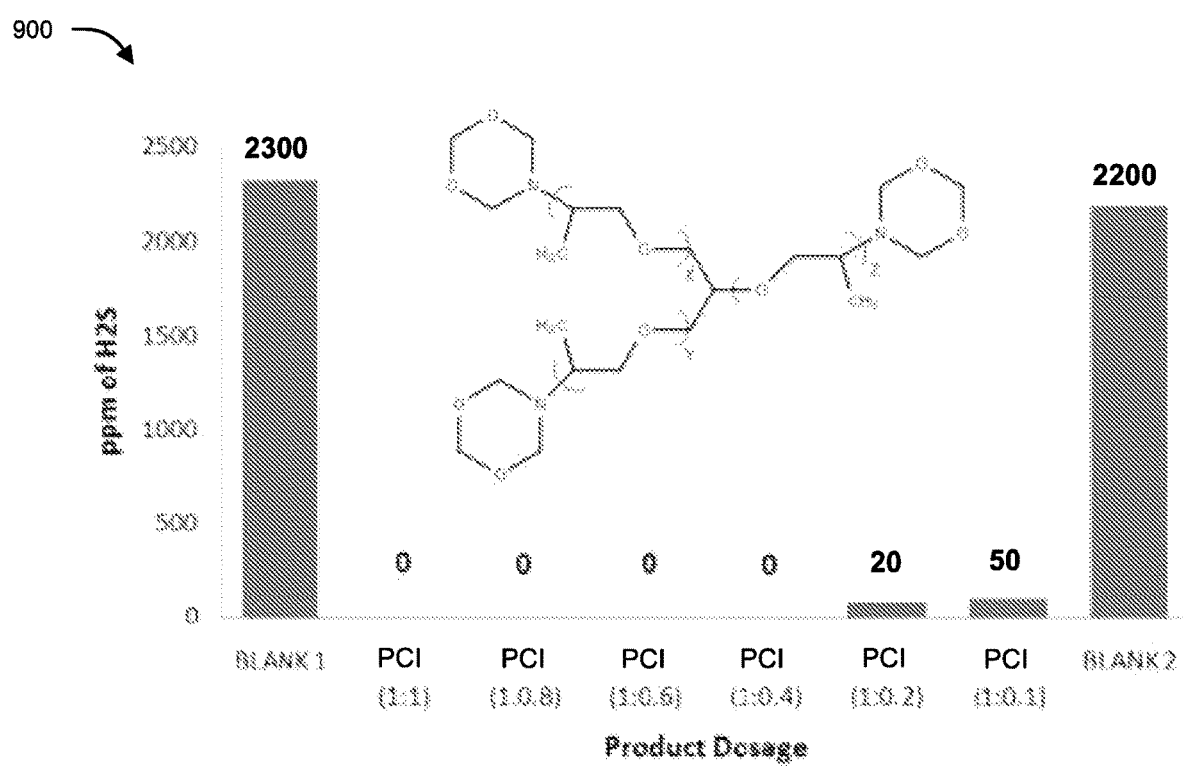
FIG. 9 is a graph illustrating H$_2$S Scavenging performance of 1,3,5-dioxazine derivative of Formula X compared against blank, in accordance with embodiments of the present disclosure.

The following is a detailed description of embodiments of the present disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Unless the context requires otherwise, throughout the specification which follow, the word "comprise" and variations thereof, such as, "comprises" and "comprising" are to be construed in an open, inclusive sense that is as "including, but not limited to."

In the following description, numerous specific details are set forth in order to provide a thorough understanding of embodiments of the present invention. It will be apparent to one skilled in the art that embodiments of the present invention may be practiced without some of these specific details.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms as used herein. To the extent a term used in a claim is not defined below, it should be given the broadest definition persons in the pertinent art have given that term as reflected in printed publications and issued patents at the time of filing.

Aspects of the present disclosure relate to 1,3,5-dioxazine derivatives capable of reducing or eliminating hydrogen sulfide and other objectionable sulfides. The 1,3,5-dioxazine derivatives realized in accordance with embodiments of the present disclosure can find utility as "sulfide scavenger" in variety of applications including, in production and/or processing of oil field produced hydrocarbons such as crude oil, petroleum, fuel oil, gasoline, diesel, liquid propane, liquid butane and the likes, in production and/or processing of syngas/natural gas and in aquaculture, but not limited thereto. In an aspect, the present disclosure provides a 1,3,5-dioxazine derivative having a structure of formula (I):

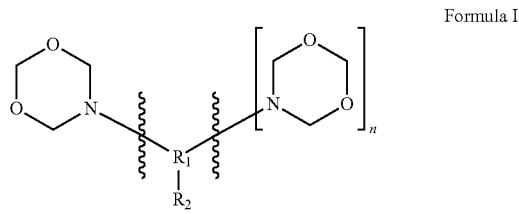

Formula I wherein:
"n" is a numeral from 0 to 10;
$R_1$ is substituted or unsubstituted amine group; or a substituted or unsubstituted, linear or branched, cyclic or acyclic $C_2$ to $C_{20}$ alkyl, $C_2$-$C_{28}$ thioether, $C_2$-$C_{28}$ alkanol, $C_2$-$C_{28}$ phosphorous containing alkyl or $C_2$-$C_{28}$ ether group; or a substituted or unsubstituted aromatic or heteroaromatic group; and
$R_2$ is H, —OH, —SH, —NH$_2$, linear or branched $C_1$-$C_{15}$ alkyl group, aromatic, heteroaromatic, bridged ring, cycloalkyl, heteroalkyl, alkyl aromatic or a 1,3,5-dioxazine group.

In an embodiment, the present disclosure provides a 1,3,5-dioxazine derivative compound of formula I, wherein 'n' is 1, $R_1$ is —N—(CH$_2$—CH$_2$)$_3$ and $R_2$ is 1,3,5-dioxazine. The compound can be chemically represented as tris(2-(1,3,5-dioxazinan-5-yl)ethyl)amine and have a structure of formula II:

Formula II

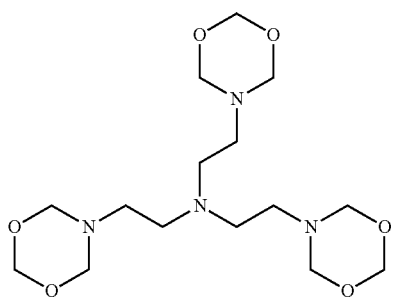

In an embodiment, the compound of formula I can have a structure as provided in formula III:

Formula III

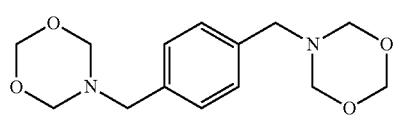

In an embodiment, the compound of formula I can have a structure as provided in formula IV:

Formula IV

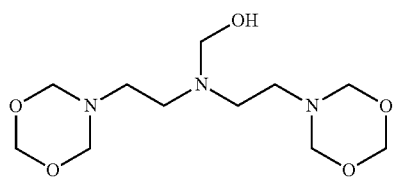

In an embodiment, the compound of formula I can have a structure as provided in formula V:

Formula V

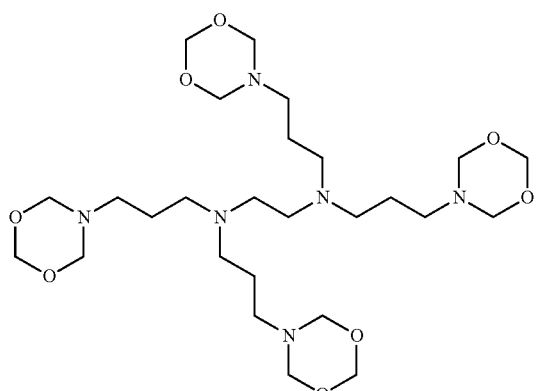

In an embodiment, the compound of formula I can have a structure as provided in formula VI:

Formula VI

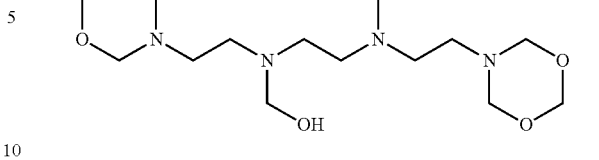

In an embodiment, the compound of formula I can have a structure as provided in formula VII:

Formula VII

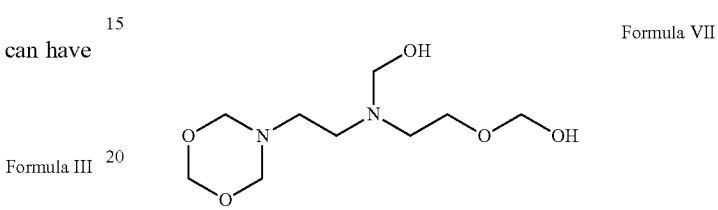

In an embodiment, the compound of formula I can have a structure as provided in formula VIII, wherein x is a numeral ranging from 0 to 10.

Formula VIII

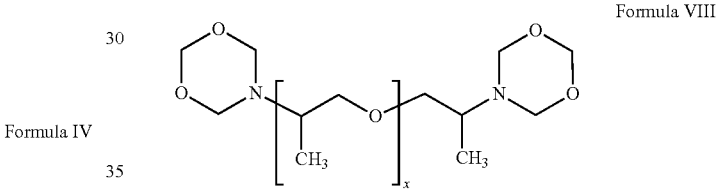

In an embodiment, the compound of formula I can have a structure as provided in formula IX, wherein x is a numeral ranging from 0 to 10.

Formula IX

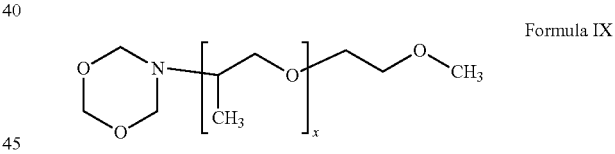

In an embodiment, the compound of formula I can have a structure as provided in formula X, wherein x, y and z, independently, represents a numeral ranging from 0 to 10.

Formula X

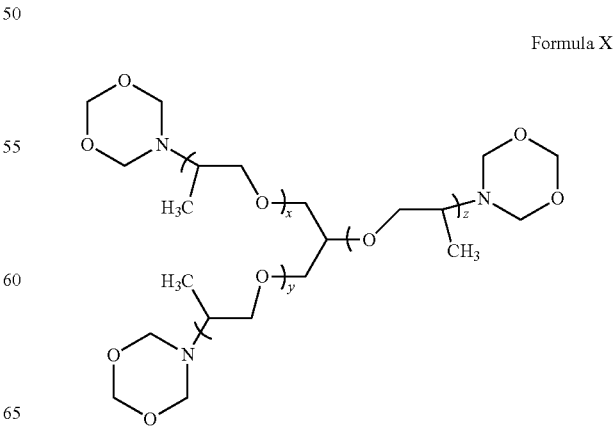

The disclosed 1,3,5-dioxazine derivative of formula I can be used for scavenging nucleophiles such as, but not limited to, hydrogen sulfide and alkyl/aryl mercaptans in oil field produced hydrocarbon fluids. Examples of oil field produced hydrocarbon fluids can include, but not limited to crude oil, crude petroleum, petroleum, fuel oil, gasoline, diesel, kerosene, liquid propane and liquid butane. The 1,3,5-dioxazine derivatives can also find utility as "sulfide scavenger" in production and/or processing of syngas/natural gas and in aquaculture. Accordingly, one should appreciate that the 1,3,5-dioxazine derivatives as realized in accordance with embodiments of the present disclosure can find myriad of applications where quenching/scavenging of sulfides and/or other sulfur derivatives/compounds is required, as known to or appreciated by a person skilled in the art without departing from the scope and spirit of the present disclosure.

In another aspect, the present disclosure provides a method for preparing the 1,3,5-dioxazine derivative of formula (I), the method including the step of reacting at least one amine compound with any or a combination of formaldehyde and paraformaldehyde under conditions effective to obtain the compound of formula (I). In an embodiment, the method for preparing the 1,3,5-dioxazine derivative of formula (I) comprises reacting at least one amine compound with an aqueous solution containing a concentration of formaldehyde under conditions effective to obtain the compound of formula (I). In an embodiment, the method for preparing the 1,3,5-dioxazine derivative of formula (I) comprises reacting at least one amine compound with an aqueous solution containing a concentration of paraformadehyde under conditions effective to obtain the compound of formula (I).

In an embodiment, the amine compound that can be utilized in the methods of the present disclosure for the preparation of 1,3,5-dioxazine derivative of formula I can be any or a combination of 1,2-diaminoethane, 1,3-Diaminopropane, 1,4-Diaminobutane, 1,4-Phenylenedimethanamine, N,N-Bis(2-aminoethyl)-1,2-ethanediamine, Diethylenetriamine, triethylenetetramine, polyalkylamines and mixture of various aliphatic, alicycic, cyclic and aromatic amines and derivatives thereof.

In an embodiment, aqueous formaldehyde, paraformaldehyde or a combination thereof having concentration in the range of 5 to 50% can be used in the methods of the present disclosure for the preparation of 1,3,5-dioxazine derivative of formula I. However, one would appreciate that any other aldehyde as known to appreciated by a person skilled in the art can be utilized to the serve the purpose as laid down in embodiments of the present disclosure without departing from the scope and spirit of the present disclosure.

In some embodiments, the molar ratio of the amine compound to the aqueous formaldehyde for one —NH$_2$ moiety can range from 1:1 to 1:20. However, utilization of any other molar ratio of the amine compound is completely within the scope and spirit of the present invention.

In an embodiment, the 1,3,5-dioxazine derivative of formula I can be prepared by slowly adding an aqueous solution of any or a combination of formaldehyde and paraformaldehyde to at least one amine compound under vigorous stirring over a period of from 30 min to 2 hours to form a reaction mixture, and then maintaining the resulting mixture under stirring for 4 to 30 hours, preferably 10 to 14 hours at room temperature to form the 1,3,5-dioxazine derivative of formula I. In an embodiment, the amine compound and the aqueous formaldehyde and/or paraformaldehyde can be mixed at a temperature ranging from 0 to 80° C., preferably 0 to 20° C., more preferably from 0 to 5° C. to form the reaction mixture. The compound of formula I thus produced may be isolated from the reaction mixture or the reaction mixture containing the compound of formula I can be directly used as nucleophile (e.g. sulfur) scavenger without isolation. In an embodiment, the 1,3,5-dioxazine derivative of formula I can be isolated by distilling off excess formaldehyde and water from the reaction mixture. The distillation can be carried out under reduced pressure at 10-80° C., preferably 40-50° C.

In an embodiment, the reaction mixture containing the compound of formula I can be diluted with water or any other solvent/liquid such as, but not limited to, polyethyleneglycols, polypropyleneglycols, other water miscible solvents like ethanol, propanol, butanol, dimethylformamide, dioxane, dimethylsulfoxide and combination thereof to produce a composition containing the desired concentration of compound of formula I. In an embodiment, the reaction mixture containing the compound of formula I can be diluted with water to make 1-99% active formulation of compound of formula I. In a preferred embodiment, the reaction mixture containing the compound of formula I can be diluted with sufficient quantity of water to make 40% active formulation of compound of formula I. In an embodiment, the composition further includes one or a combination of additives as known to or appreciated by a person skilled in the art to arrive at the desired formulation.

In an embodiment, the tris(2-(1,3,5-dioxazinan-5-yl)ethyl)amine of formula II can be prepared as outlined in the following scheme I:

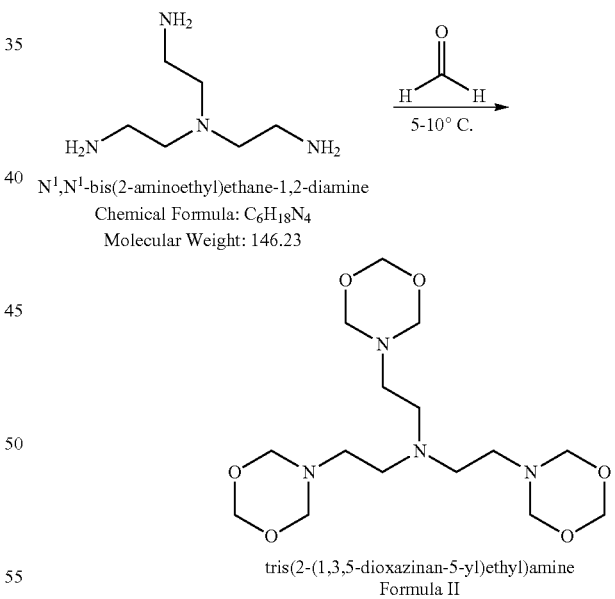

In another aspect, the present disclosure provides a method for reducing the amount of or eliminating hydrogen sulfide or alkyl/aryl mercaptan from a medium. The method includes contacting the medium with an effective amount of a compound of formula (I) of the present disclosure. In an embodiment, the medium is oil field produced hydrocarbon fluid. In another embodiment, the medium is aquaculture. In another embodiment, the medium is syngas or a natural gas.

In an embodiment, the method for reducing the amount of or eliminating hydrogen sulfide or alkyl/aryl mercaptan from a medium comprises contacting the medium with an effective amount of a compound of formula (I) of the present disclosure for a time ranging from about 5 seconds to about 240 minutes. However, a person skilled in the art would appreciate that the compound of Formula 1 can be contacted with the medium for any length of time to serve the purpose, as laid down in embodiments of the present disclosure, without departing from the scope and spirit of the present invention.

In an embodiment, 0.001 to 10% by weight of the compound of formula I can be added to an oil field produced hydrocarbon fluid to remove hydrogen sulfide or alkyl/aryl mercaptan there from. However, a person skilled in the art would appreciate that any other concentration of the compound of Formula 1 can be utilized to serve the purpose, as laid down in embodiments of the present disclosure, without departing from the scope and spirit of the present invention.

In an embodiment, the method for reducing the amount of or eliminating hydrogen sulfide or alkyl/aryl mercaptan from a medium comprises contacting the medium with an effective amount of a compound of formula (I) of the present disclosure at a temperature ranging from about 0° C. to about 90° C. In an embodiment, the method comprises contacting the medium with an effective amount of a compound of formula (I) at a temperature ranging from about 25° C. to about 60° C. However, a person skilled in the art would appreciate that the compound of Formula 1 can be contacted with the medium at any other temperature to serve the purpose, as laid down in embodiments of the present disclosure, without departing from the scope and spirit of the present invention.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Preparation of
tris(2-(1,3,5-dioxazinan-5-yl)ethyl)amine of
Formula II

Example 1: Preparation of
tris(2-(1,3,5-dioxazinan-5-yl)ethyl)amine Using
37% Aqueous Formalin 20 Lit pilot scale glass reactor, attached with condenser, thermometer and mechanical stirrer, was charged with, 1462 gm of N,N-Bis(2-aminoethyl)ethane-1,2-diamine and stirred at 5-10° C. till it achieves the bath temperature. 8100 gm, of 37% aqueous formaldehyde, previously cooled at 0° C. was charged through dropping funnel over the period of 2-4 hours. Aqueous formaldehyde being used can have the concentration ranging from 5-50%. The process comprising admixing amine and aqueous formaldehyde was carried out at temperature ranging from 0-20° C., preferably between 0-5° C. Slight exotherm was observed during initial addition of formaldehyde to amine, from 5° C. to 40° C., which can be controlled using external cooling to the reactor. In the reaction between amine and formaldehyde, amine to formaldehyde ratio for one $NH_2$ group is 3-6. After complete addition of the formaldehyde solution, reaction mixture was allowed to stir at room temperature over 15 hours. Excess formaldehyde from the product was removed by distillation of the reaction mixture under reduced pressure, which affords thick orange colored compounds free of excess formalin. This step of distilling was carried out at reduced pressure at 10-80° C., and more specifically at 40-50° C. Finally product was weighed in packaging drum and diluted with water with 2.5 times the volume to make 40% active formulation of the product.

Example 2: Preparation of
tris(2-(1,3,5-dioxazinan-5-yl)ethyl)amine Using
Paraformaldehyde 10 Lit pilot scale glass reactor, attached with condenser, thermometer and mechanical stirrer, was charged with, 1462 gm of N,N-Bis(2-aminoethyl)ethane-1,2-diamine followed by addition of 5538 gm of water and stirring at 5-10° C. till it achieves the bath temperature. 3000 gm, of Paraformaldehyde, was added portion wise over the period of 4 hours. Slight exotherm was observed during initial addition of Paraformaldehyde to amine, from 5° C. to 40° C., which can be controlled using external cooling to the reactor. After complete addition of the Paraformaldehyde, reaction mixture was allowed to stir at room temperature over 15 hours. Excess formaldehyde from the product was removed by distillation of the reaction mixture under reduced pressure, which affords thick orange colored compound free of excess formalin. This step of distilling was carried out at reduced pressure at 10-80° C., and more specifically at 40-50° C. Finally product was weighed in packaging drum and diluted with water with 2.5 times the weight volume to make 40% active formulation of the product.

Example 3: Hydrogen Sulfide Scavenging Capacity
Test

The compounds of formula II, III, IV, V and VI were tested for their application as hydrogen sulfide scavenger using ASTM D5705 test method. ASTM D5705 is a Standard Test Method for Measurement of Hydrogen Sulfide in the Vapor Phase above Residual Fuel Oils. In typical testing, Exxsol D80 solvent was used as test solvent which was saturated with hydrogen sulfide gas with specified pressure and time in glass bottles. $H_2S$ saturated Exxsol D80 was closed properly and allowed to stand at 60° C. for 2 hours. Vapour phase $H_2S$ was measured using Dragger Tube fixed inside rubber cork at one end and a pump at other end, to effectively suck all the vapour phase $H_2S$. Similarly, for testing the performance of the compounds, after saturation step different dosages of chemicals under discussion were added before closing the bottle. Typical dosages of the compounds with respect to concentration of $H_2S$ (observed in blank) were 1:1, 1:0.8, 1:0.6, 1:0.4, 1:0.2 and 1:0.1. As an example, if the blank reading comes as 3000 ppm, for 1:1 dosage, 3000 ppm of claimed chemicals as 40% active solution was added, and so on.

Figure 10:
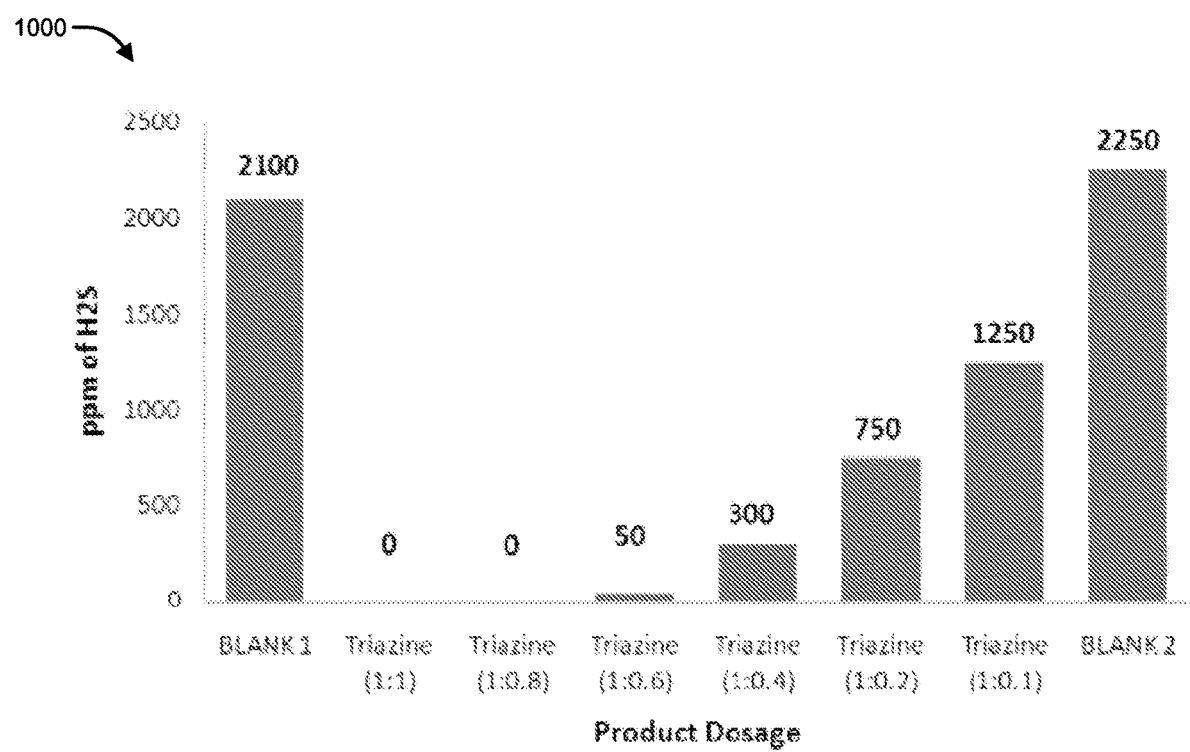
FIG. 10 is a graph illustrating H$_2$S Scavenging performance of traditional triazine based product (40% active formulation) compared against blank, in accordance with embodiments of the present disclosure.
Figure 11:
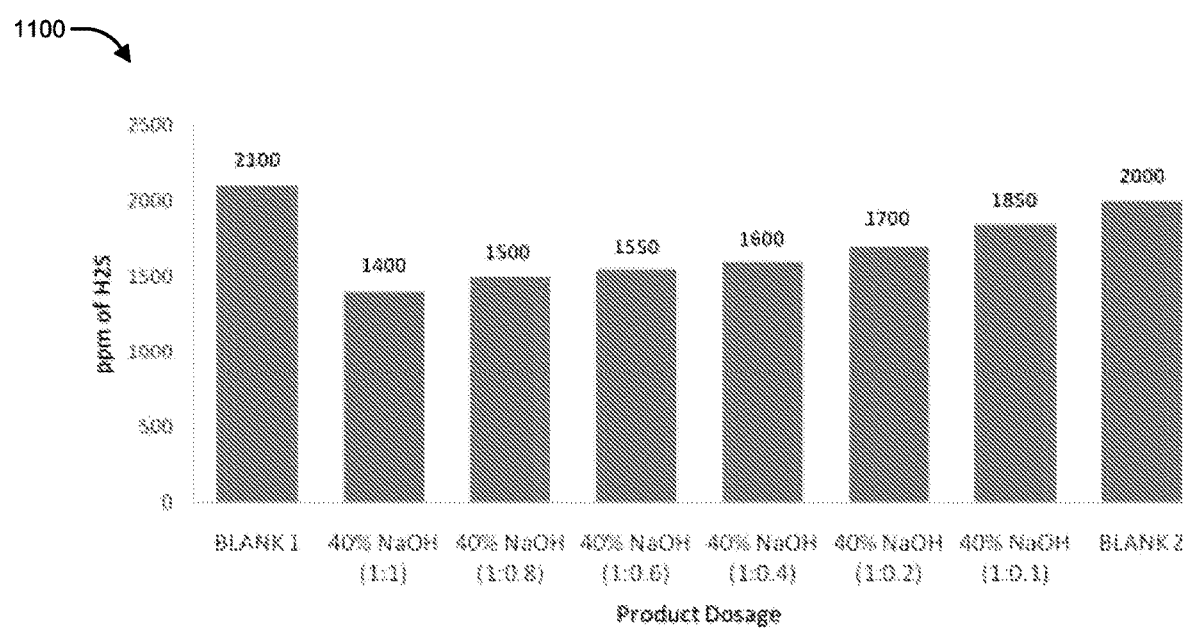
FIG. 11 is a graph illustrating H₂S Scavenging performance of 40% aqueous NaOH solution compared against blank, in accordance with embodiments of the present disclosure.

The compounds of formula II to X were prepared as 10% to 80% active formulations and treated with the test solvent to determine the sulfide scavenging capacity of these compounds. Untreated blank samples were used to compare and determine the scavenging capacity of these compounds. The results of these capacity tests are presented in FIGS. 1 to 9. Further, the hydrogen scavenging performance of compounds of formula II to X was compared against conventional triazine scavengers and 40% NaOH solution. The results of this comparison tests are presented in FIGS. 10 and 11. The comparison tests (FIGS. 10 and 11) demonstrate the effectiveness of the compounds of the present disclosure over conventional triazine scavengers and NaOH solution under a variety of treating conditions and concentrations. FIGS. 1 to 9 reveal that the 1,3,5-dioxazine derivatives/compounds of formula I is more effective in scavenging hydrogen sulfide, and it is significant to note that the compounds of formula II to X were much more effective than the conventional triazine scavengers and NaOH solution due to the presence of at least two reactive (active) methylene groups.

ADVANTAGES OF THE INVENTION

The present disclosure provides 1,3,5-dioxazine derivative of formula I capable of reducing or eliminating hydrogen sulfide and other objectionable sulfides.

The present disclosure provides 1,3,5-dioxazine derivative of formula I which is much more effective than the conventional triazine based scavengers and aqueous NaOH solution.

The present disclosure provides 1,3,5-dioxazine derivative of formula I which is easy to produce and highly economical.

The present disclosure provides a process for preparing 1,3,5-dioxazine derivative of formula I that can be safely and easily scaled up.

The present disclosure provides a process for preparing 1,3,5-dioxazine derivative of formula I, that is simple and commercially viable.

The present disclosure provides a sulfide scavenger which overcomes the disadvantages associated with the prior art scavengers.

I claim:

1. A method for preparing a compound selected from the group consisting of:

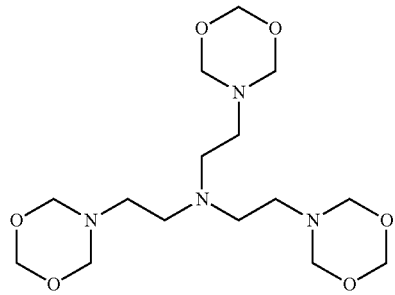

Formula II

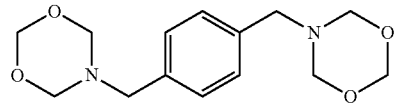

Formula III

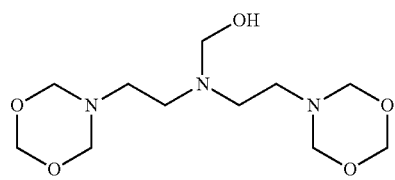

Formula IV

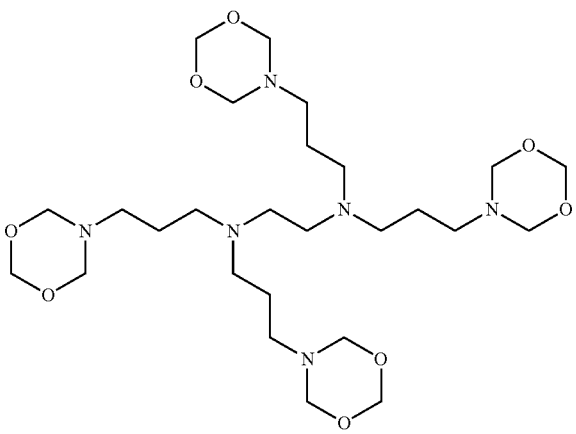

Formula V

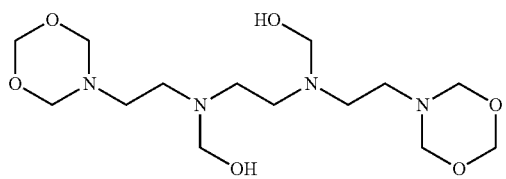

Formula VI

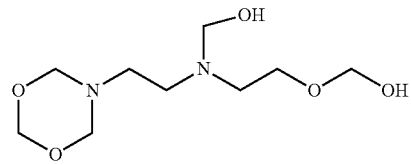

Formula VII

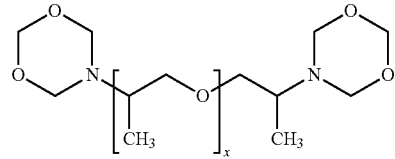

Formula VIII

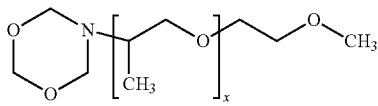

Formula IX

Formula X

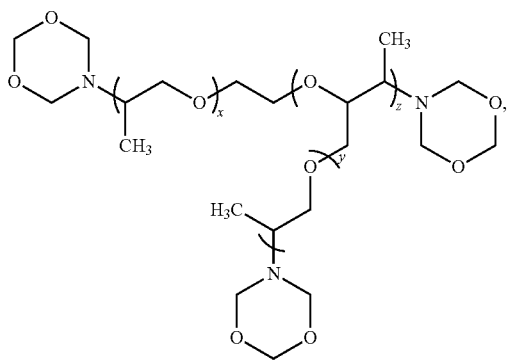

and wherein, x, y and z independently represent a numeral ranging from 0 to 10, wherein the method comprises reacting at least one amine compound with any or a combination of aqueous formaldehyde and paraformaldehyde to obtain said compound.

2. The method according to claim 1, wherein the at least amine compound is selected from any or a combination of 1, 2-diaminoethane, 1,3-Diaminopropane, 1,4-Diaminobutane, 1, 4-Phenylenedimethanamine, N, N-Bis(2-aminoethyl)-1, 2-ethanediamine, Diethylenetriamine, triethylenetetramine, polyalkylamines and derivatives thereof.

3. The method according to claim 1, wherein the any or a combination of aqueous formaldehyde and paraformaldehyde has a concentration ranging from 5 to 50%.

4. The method according to claim 1, wherein a molar ratio of the at least one amine compound to the any or a combination of aqueous formaldehyde and paraformaldehyde for one —NH$_2$ group ranges from about 1:1 to about 1:20.

5. A method for reducing hydrogen sulfide or alkyl/aryl mercaptan in a medium, the method comprising contacting the medium with an effective amount of a compound selected from the group consisting of:

Formula II

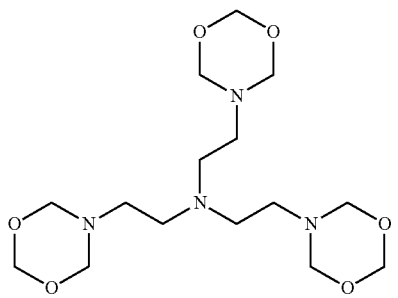

Formula III

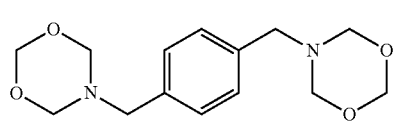

Formula IV

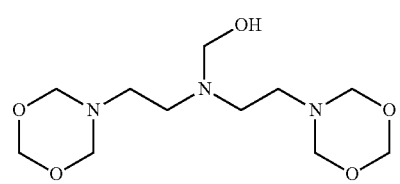

Formula V

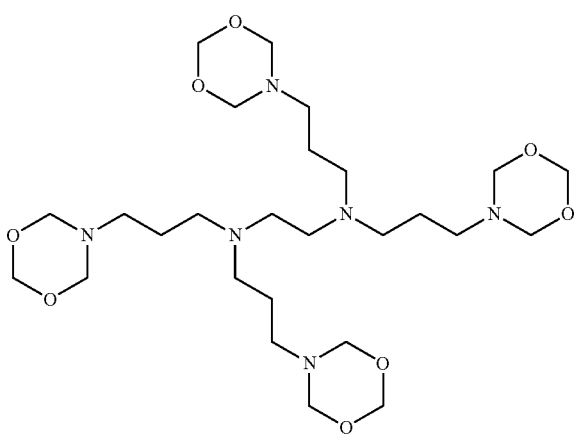

Formula VI

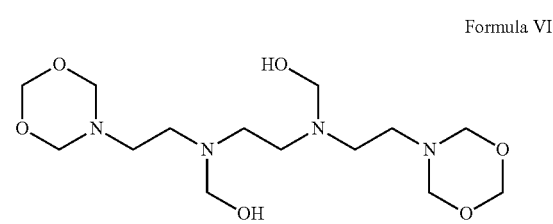 [SMILES: OCN(CCN(CO)CCN1COCOC1)CCN1COCOC1]

Formula VII

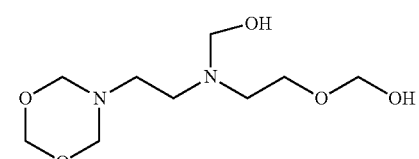

Formula VIII

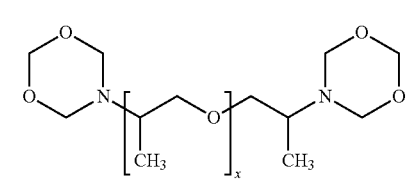

Formula IX

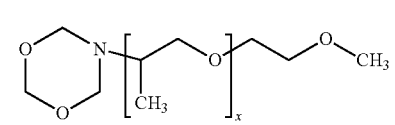

-continued

Formula X

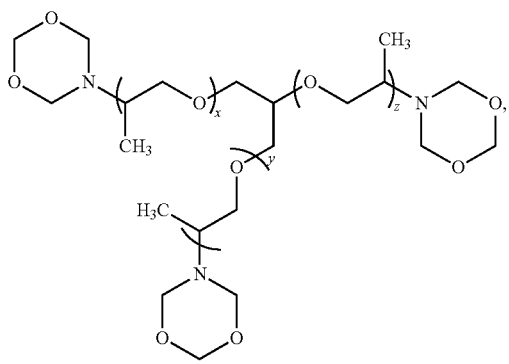

and
wherein, x, y and z independently represent a numeral ranging from 0 to 10.

6. The method as claimed in claim 5, wherein said medium is a hydrocarbon fluid, a natural gas, or an aquaculture.

7. The method as claimed in claim 5, wherein said step of contacting the medium with the effective amount of the compound is carried out at a temperature ranging from about 0° C. to about 90° C.

8. The method as claimed in claim 5, wherein said step of contacting the medium with the effective amount of the compound is carried out for a length of time ranging from about 5 seconds to about 240 minutes.

9. The method as claimed in claim 5, wherein said medium is a hydrocarbon fluid.

10. The method as claimed in claim 9, wherein said hydrocarbon fluid is an oil field produced hydrocarbon fluid.

11. The method as claimed in claim 5, wherein said compound is

Formula II

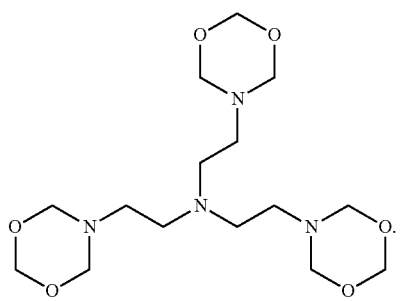

12. The method as claimed in claim 5, wherein said compound is

Formula IV

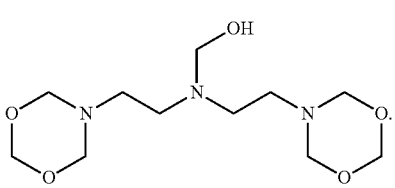

13. The method as claimed in claim 9, wherein said compound is

Formula II

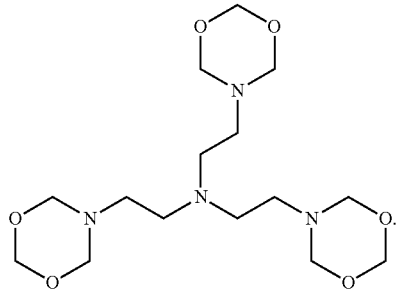

14. The method as claimed in claim 1, wherein said compound is selected from the group consisting of:

Formula II

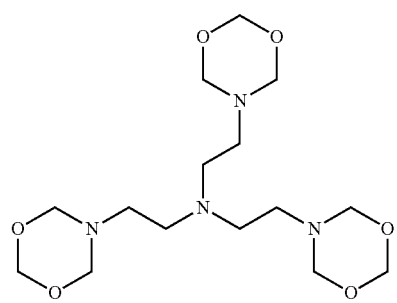

Formula III

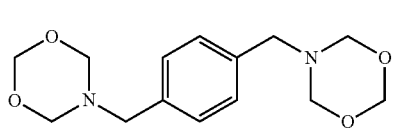

Formula IV

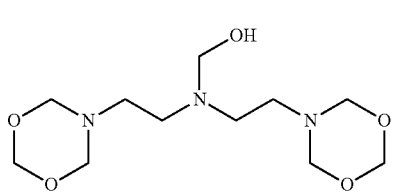

Formula V

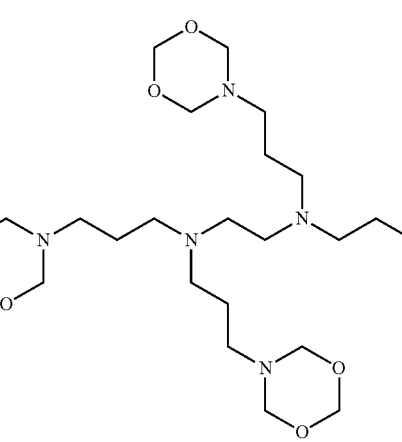

Formula VI
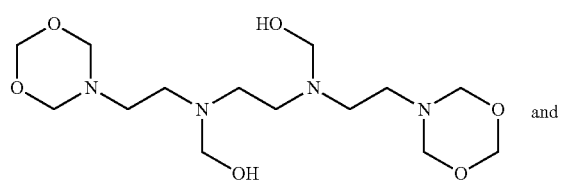
and
Formula VII
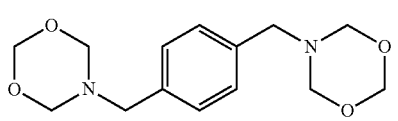
15. The method as claimed in claim 5, wherein said compound is selected from the group consisting of:
Formula II
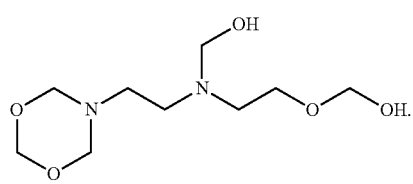
Formula III
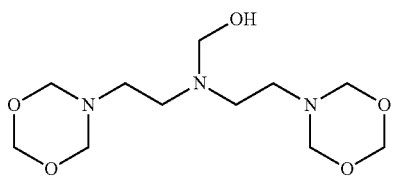
Formula IV
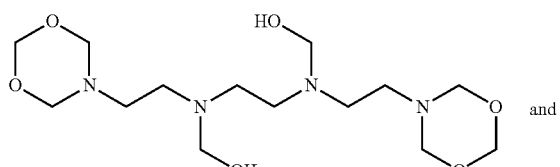
Formula V
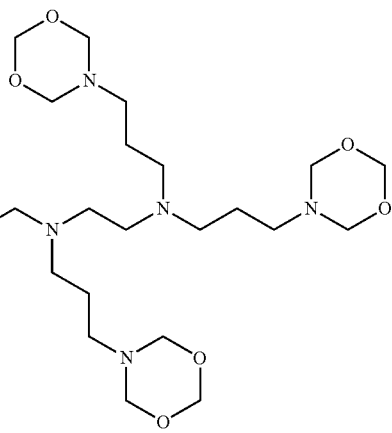
Formula VI
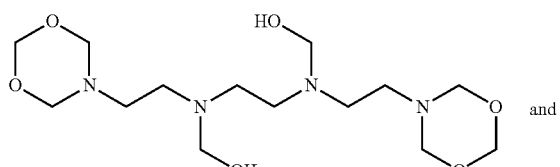
and
Formula VII
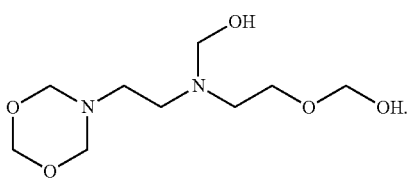
* * * * *